(12) United States Patent
Low (10) Patent No.: US 6,515,494 B1
(45) Date of Patent: Feb. 4, 2003

(54) SILICON WAFER PROBE STATION USING BACK-SIDE IMAGING

(75) Inventor: Frank J. Low, Tucson, AZ (US)

(73) Assignee: Infrared Laboratories, Inc., Tucson, AZ (US)

(*) Notice: Subject to any disclaimer, the term of this patent is extended or adjusted under 35 U.S.C. 154(b) by 0 days.

(21) Appl. No.: 09/618,607

(22) Filed: Jul. 17, 2000

(51) Int. Cl.[7] .............................................. G01R 31/00

(52) U.S. Cl. ..................... 324/752; 324/765; 324/750; 324/501

(58) Field of Search .......................... 250/318; 324/752, 324/765, 750, 501

(56) References Cited

U.S. PATENT DOCUMENTS

| | | | | |
|---|---|---|---|---|
| 5,493,236 A | * | 2/1996 | Ishii et al. ................... | 324/752 |
| 5,783,835 A | * | 7/1998 | Hollman et al. ....... | 250/559.46 |
| 6,086,453 A | * | 7/2000 | Fukuoka et al. ............... | 45/15 |

OTHER PUBLICATIONS

Steve Seidel et al., "Application of Infrared Emission Microscope for Flip–Chip (C4) Failure Analysis," Conf. Proc. for 25th ISTFA, Nov. 1999, pp. 471–476.

* cited by examiner

Primary Examiner—Kiet T. Nguyen
(74) Attorney, Agent, or Firm—Antonio R. Durando; Durando Birdwell & Janke, PLC (57) ABSTRACT

A back-side imaging infrared microscope is integrated with a novel integrated-circuit probe station. The microscope is located below the silicon substrate of the integrated circuit, on the side opposite to the probe card. The electronic circuitry located on the top side of the substrate is imaged through the back side of the substrate and through a window sized to provide a view of a single integrated circuit and of the corresponding probe tips overlying the contact pads. Since the silicon substrate of integrated circuits is transparent to infrared wavelengths, the alignment between probe tips and contact pads is carried out with a clear view of both from the bottom of the substrate. Furthermore, emission images from the integrated circuit are taken during testing with the same microscope after electrical contact has been established.

20 Claims, 8 Drawing Sheets

SILICON WAFER PROBE STATION USING BACK-SIDE IMAGING

BACKGROUND OF THE INVENTION

1. Field of the Invention

This invention is related in general to the field of electronic microscopes and cameras for testing integrated circuits in wafer or chip form. In particular, the invention concerns the use of an infrared microscope for imaging and aligning the probe tips of a conventional probe card with the electrical contact pads of the integrated circuit. It also enables more advanced probe cards to be used with flip-chip technology.

2. Description of the Related Art

Conventional testing of integrated circuits (ICs) is carried out on an individual IC at the wafer level by contacting the electrical contact pads of the IC with the finger tips of a probe card facing the top side of the circuit. The probe card energizes the circuit and performs diagnostic tests that enable the detection of faults, which may then be specifically identified with further testing performed on individually mounted chips. For example, recent advances in the art have been obtained by using an infrared (IR) microscope to image hot-carrier emission and black-body radiation caused by circuit failures. These failures can be viewed directly by imaging the integrated circuit with light of infrared wavelength. See, for example, Steve Seidel et al., "Application of Infrared Emission Microscope for Flip-Chip (C4) Failure Analysis," Conf. Proc. for 25th ISTFA, November 1999, pp. 471–476. Thus, the full power of IR microscopy has been limited to packaged parts.

During the process of establishing the electrical contacts required for testing of a chip, the tips of the probe card must first be aligned vertically over the contact pads of the integrated circuit, and then the probe tips are lowered and pressed against the pads to establish contact. In order to implement the initial alignment, conventional equipment utilizes a visible-light camera adapted to view the pads and probe tips through a top-side viewing port in the probe card; contact between corresponding probe tips and IC pads is then ensured by overcoming with sufficient downward pressure any horizontal misalignment resulting from a tip or tilt of the probe card with respect to the underlying chip.

Several disadvantages characterize this prior-art approach. As one skilled in the art would readily recognize, the tips of the contact fingers of a probe card are curved vertically downward after an initial radial extension inward from the edge of the viewing port; thus, the tips are not all clearly visible to an imaging device placed substantially vertically above the viewing port. Therefore, the vertical alignment of the probe tips with the IC contact pads is not as precise as it would be if the tips were imaged in their entirety. In addition, current top-side imaging is limited to contact pads that are positioned at the edges of the integrated circuit in order to provide room for the viewing port through the probe card. Thus, recently introduced "flip-chip" probe cards, which have probe tips designed to match contact pads located throughout the interior of the chip, cannot be aligned with conventional top-side imaging.

The relative lack of access to a clear view of all probe tips afforded by the prior art also prevents a determination of their precise spatial position and an adjustment of their planar attitude with respect to the plane of the IC contact pads. As a result, the electrical contact between all probe-pad pairs is ensured only by lowering the probe card a sufficient distance to cause the union of even the most distant pairs. Obviously, any such horizontal misalignment (that is, lack of parallelism) between the planes of the probe tips and the IC contact pads causes an uneven distribution of the downward force exerted by the probe card on the IC substrate, which may adversely affect the proper performance of the circuit. Most importantly, though, the pressure required to overcome such misalignments may cause the circuit's silicon substrate to bend and possibly be damaged. In the case of thinned wafers that are not properly supported, these excess forces can break the wafer.

In view of these shortcomings of current IC testing apparatus and procedures, there is still a need for a device that permits the precise, relatively stress-free, alignment of all types of probe cards, including flip-chip cards with more rigid probe tips, with integrated circuits in wafer form. The present invention is based on back-side imaging of the integrated circuit and the probe tips with an infrared microscopic device capable of viewing both from the bottom of the IC silicon substrate. Since packaged parts will suffer additional failures, the apparatus must retain its ability to mount and analyze packaged parts.

BRIEF SUMMARY OF THE INVENTION

The primary objective of this invention is a fast and precise system for aligning the contact pads of an integrated circuit with corresponding probe tips in a probe card, regardless of the position of the pads within the circuit and of access from the top side of the card.

Another goal of this invention is a device and an associated procedure that provide adequate support of the wafer while providing a viewing window large enough to image the IC under test.

Another goal of the invention is a device and an associated procedure that minimizes the pressure exerted by the probe tips over the integrated circuit, so as to avoid bending of its substrate and any damage that may otherwise result from structural stresses.

Another objective is an apparatus suitable for carrying out both the alignment of the integrated circuit with the probe card and the normal testing of the circuit in a single operation.

Another object is an apparatus suitable for testing integrated circuits both in the form of a packaged chip and in the form of a wafer.

Still another object is an approach suitable for automated implementation, so that multiple tests can be carried out with speed and reliability for quality control of several integrated circuits in a water.

Another goal is also a method and apparatus that are suitable for incorporation within existing instruments.

A final objective is a system that can be implemented easily and economically according to the above stated criteria.

Therefore, according to these and other objectives, the preferred is embodiment of the present invention includes a back-side imaging infrared microscope combined with a conventional integrated-circuit probe card mounted on a platen that lowers the probe card to make contact with the top side of the wafer. At the same time, the microscope is located below the silicon substrate of the integrated circuit, on the side opposite to the probe card. The back side of the substrate is imaged through a window sized to provide a view of a single integrated circuit and of the corresponding probe tips overlying the contact pads, while also providing sufficient vertical support to minimize bending of the silicon substrate. Since the silicon substrate of integrated circuits is transparent to infrared wavelengths, the alignment between probe tips and contact pads can be carried out with a clear view of both from the bottom of the substrate. Appropriate mechanisms for angular and x,y,z position adjustments of the probe card with respect to the integrated circuit enable their vertical and parallel alignment. Furthermore, emission images from the integrated circuit can be taken during testing with the same microscope after electrical contact has been established. By using a single microscope for testing and alignment from the bottom side of the silicon substrate, precise alignment becomes possible even when the entire top side of the circuit is dedicated to accommodate electrical contacts.

According to another aspect of the invention, a special supporting plate with a bottom view window is combined with a movable frame for an IC wafer. The frame is adapted for slidable, precisely controlled motion over the supporting plate, so that multiple circuits in a wafer can be positioned sequentially over the view window, aligned with the probe card, and tested by imaging infrared emissions caused by circuit failures. Thus, the full benefits of IR microscopy can be applied to integrated circuits before they are packaged. Initial detection of a fault and the subsequent failure analysis, which have been so far performed in two separate steps, are combined into a single operation by the present invention.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

The silicon material constituting the substrate of substantially all integrated circuits is transparent to wavelengths in the infrared range. Accordingly, this invention is based on the idea of utilizing an infrared camera to "see" through the silicon substrate of the integrated circuit from the bottom of the chip in order to align the contact pads with the tips of a probe card. Moreover, the same infrared camera can be used to image infrared hot-carrier and thermal emissions resulting from circuit faults for the purpose of failure analysis.

It is noted that the embodiments of the present invention are described with reference to x, y and z orthogonal coordinates wherein x and y define a horizontal plane parallel to the plane of the integrated circuit and z defines a vertical direction orthogonal to such plane, but it is obvious that the structure and operation of the features detailed herein could be rotated in any direction with equivalent results. The terms top and front are used to refer to the side of an integrated circuit exhibiting contact pads, while the terms bottom and back are used to refer to the opposite side. The terms IR microscope and IR camera are used interchangeably to refer to an infrared camera fitted with a microscope objective. Finally, the term infrared is not used to refer strictly to wavelengths above the visible range; rather, it is used for any wavelength at which a silicon wafer is sufficiently transparent to see through it with a camera operating at that wavelength. It is also understood that the various components shown in the drawings are not drawn to relative scale, but are represented only schematically for illustration.

Figure 1:
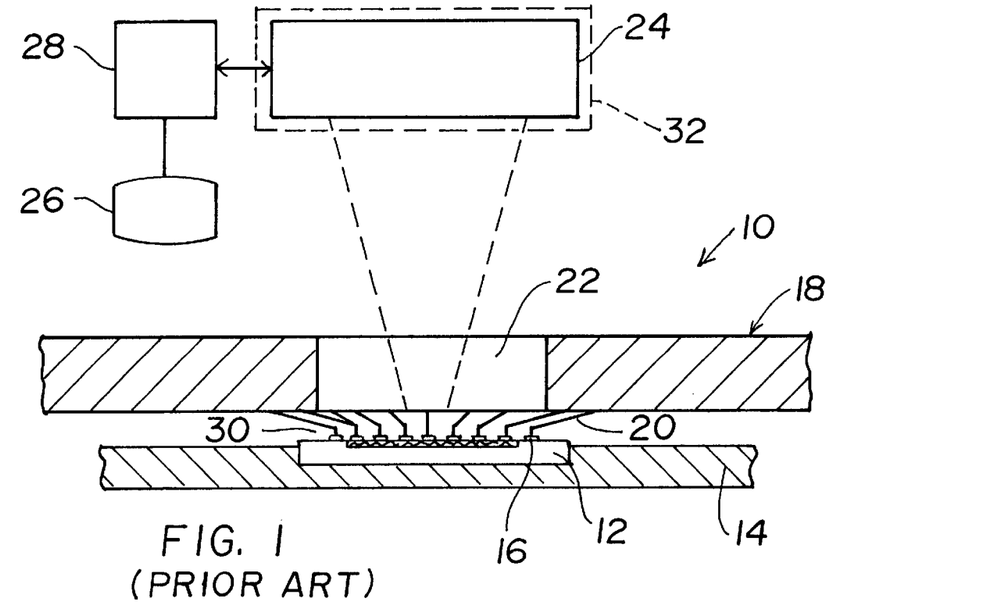
FIG. 1 is a schematic, partially sectioned, elevational representation of a prior-art IC chip testing station.

Referring to the drawings, wherein like parts are designated throughout with like numerals and symbols, FIG. 1 illustrates schematically a prior-art arrangement for aligning an IC chip with a conventional probe card prior to testing for circuit integrity or for failure analysis from the top side using a conventional camera that cannot see through silicon. The chip 12 is held on a supporting stage 14 with the contact pads 16 facing a probe card 18. Prior to testing, the probes or fingers 20 of the card are brought within vertical alignment of the pads 16 by guiding them, either manually or automatically, in response to images collected with a microscope objective through a top-side viewing port 22 contained within the perimeter of the probes 20 in the probe card 18. When vertical alignment within prescribed tolerances is achieved, the card is lowered to effect contact of the probes with the pads, as illustrated. A conventional, visible-light microscope 24 (typically equipped with a camera monitor 26 and appropriate computer-control hardware 28) focused on the pads 16 and the tips 30 of the probes is used to track the relative motion of the two and ensure proper electrical contact.

When a fault is found in a chip at the wafer level as a result of electrical testing, a more sensitive visible light camera can be used to locate emissions from the faulty circuit before packaging. However, modern IC devices require many metal layers above the silicon so that much of the circuitry is obscured forcing the IC to be packaged before it can be prepared for back-side analysis. To gain access to the back side of the packaged device, a viewing window is generated in the package. Note that flip-chip devices must always be imaged from the back side. Once the defect is located, the chip is often de-mounted for further study in a different device, normally in a laboratory environment, to identify the specific sources of failure. Another microscope 32, typically equipped with a cooled CCD camera (identified in phantom line in the figure and also connected to peripheral hardware and monitor) is typically used to carry out failure analysis while the integrated circuit is energized in a testing device similar to the set-up described in FIG. 1.

The present invention modifies the apparatus of the prior art by providing a bottom-side viewing window in the stage supporting the integrated circuit and an infrared camera designed to look upward and allow back-side imaging through the substrate of the integrated circuit. One such relatively new camera, the unit sold by Infrared Laboratories, Inc., of Tucson, Ariz., under the trademark IREM1™, operates in the 1–2.5 micron range and can detect thermal emissions as well as emissions from forward or reverse-bias-junction, latch-up, gate-oxide, and other circuit defects.

Figure 2:
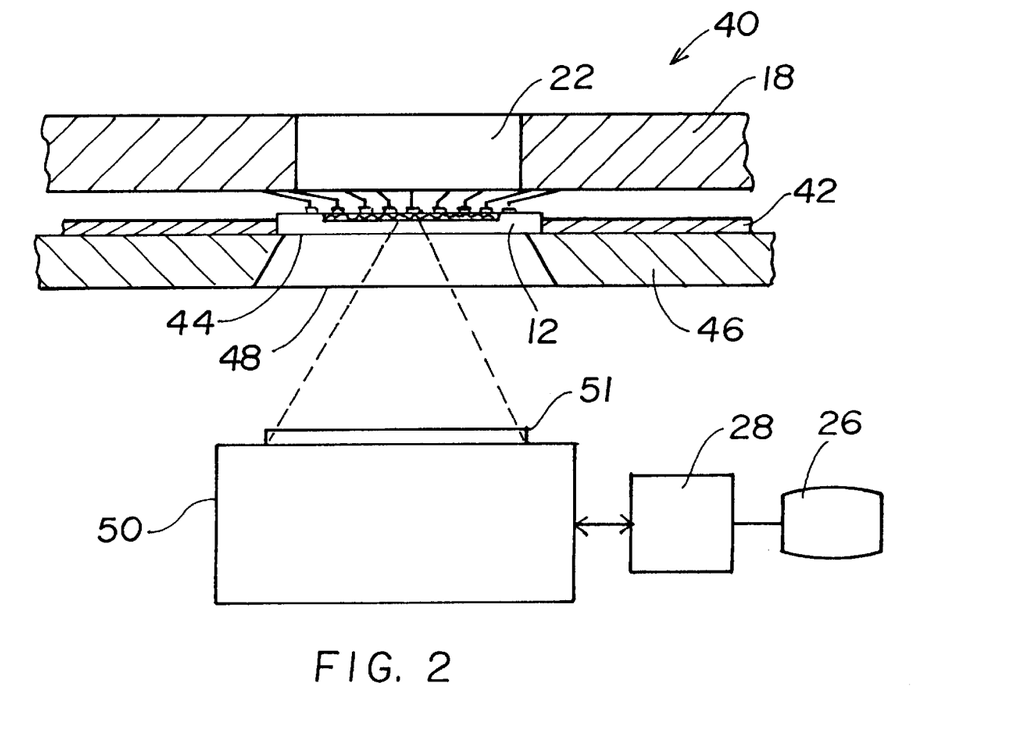
FIG. 2 illustrates the use of an infrared microscope in a modified configuration of FIG. 1 according to the present invention.

Thus, as illustrated in the schematic representation 40 of FIG. 2, the stage 42 supporting the chip 12 is provided with an opening 44 that allows a complete view of the bottom side of the silicon substrate of the chip 12. The stage 42 in turn is mounted on a flat support plate 46 with a window 48 sufficiently large to expose the entire underside of the chip. An infrared microscope 50, equipped with appropriate control computer hardware 28 and camera monitor 26, if desired, is positioned under the plate 46 and adapted to image the silicon chip from the bottom side of the silicon substrate. A source of infrared light 51 is used to illuminate the field of view of the microscope 50, so that it can be imaged by reflected light. Due to this configuration, the single IR microscope 50 is used both for aligning the tips 30 of the probes 20 with the IC contact pads 16 and for imaging faulty spots in the circuit identified by collecting infrared emission during testing. Given the transparency of the silicon layer to infrared wavelengths, the probes 20 and pads 16 can be seen and monitored during the alignment procedure to effect their pairing within the mechanical tolerances of the system. The convergence of the probes and pads can be accomplished manually through conventional x,y,z translation and angular rotation mechanisms, with the aid of a monitor or automatically, using control mechanisms and computer software that is well known in the art of microscopic metrology. Once electrical contact between the probes and pads has been established, the IR microscope 50 can then be used also to conduct failure analysis based on emissions collected from the underside of the chip.

Figure 3:
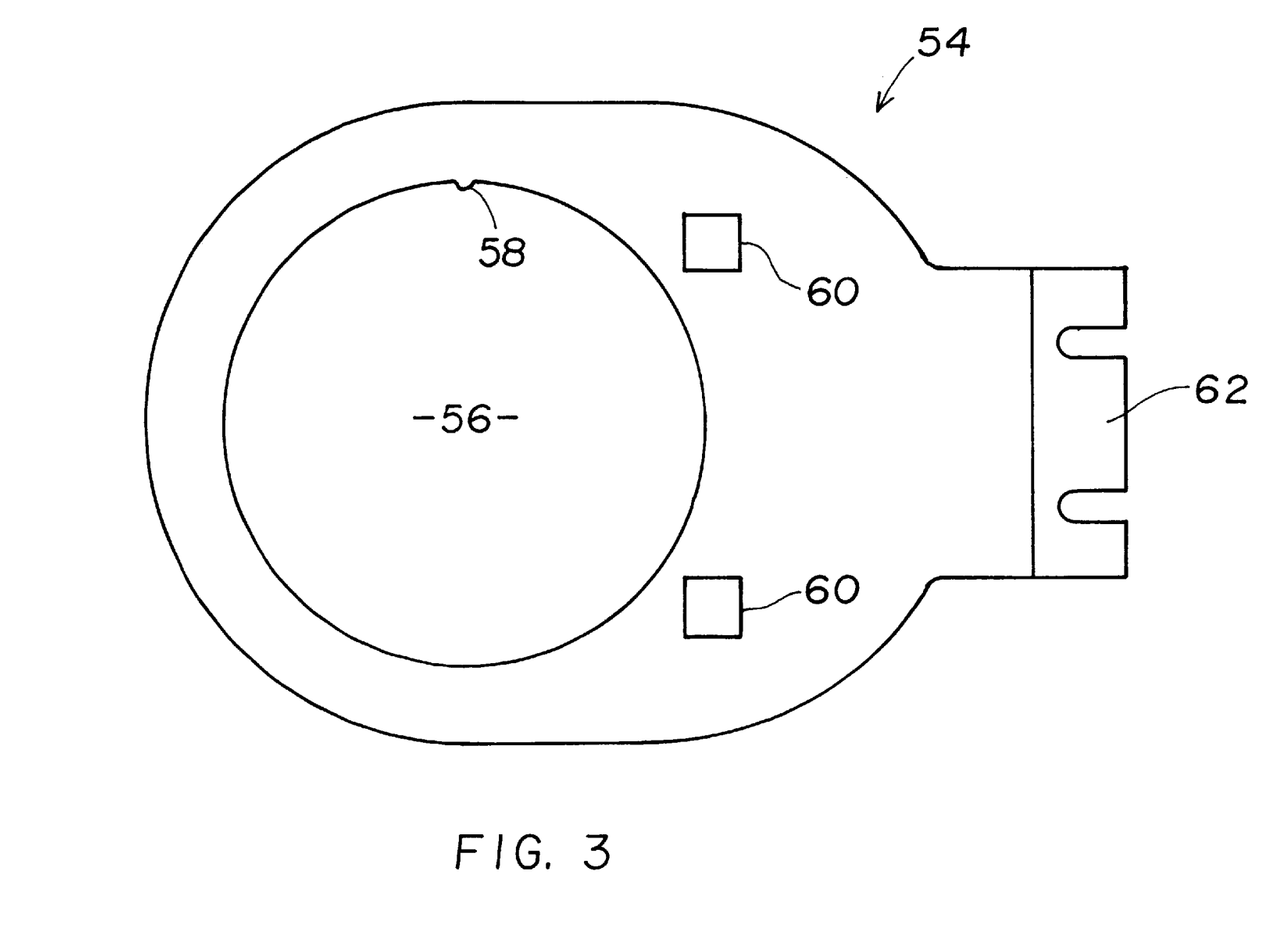
FIG. 3 is a top view of a tray used to house an IC wafer for testing in a probe station according to the invention.

Based on the concept disclosed in FIG. 2, the present invention can be extended to test integrated circuits in wafer form, so that failure analysis can be performed shortly after a fault is detected, rather than through the conventional steps of first packaging the chip and then testing it in a separate instrument. As illustrated in FIG. 3, this is accomplished by providing a wafer tray 54 that contains a through opening 56 conforming to is the shape of a conventional IC wafer, currently a disk about 200 mm in diameter and 0.2–0.7 mm thick. Accordingly, the tray 54 is preferably made from a sheet of material approximately 0.1 mm thicker than the wafer for which it is intended. A protrusion 58 from the structure of the tray into the opening 56 is provided to fit a correspondingly indented alignment notch used in silicon wafers, so that the precise position of each integrated circuit in the wafer can be readily established after insertion in the opening 56. A short flat section in the edge of the opening (not shown in the figure) can be used, instead of a protrusion, to similarly align wafers having a flat alignment notch in the border. Windows 60 are also provided in the tray in order to permit unobstructed through vision in cases when high metallization on the wafer precludes a clear view of the probe card for alignment purposes.

Figure 4:
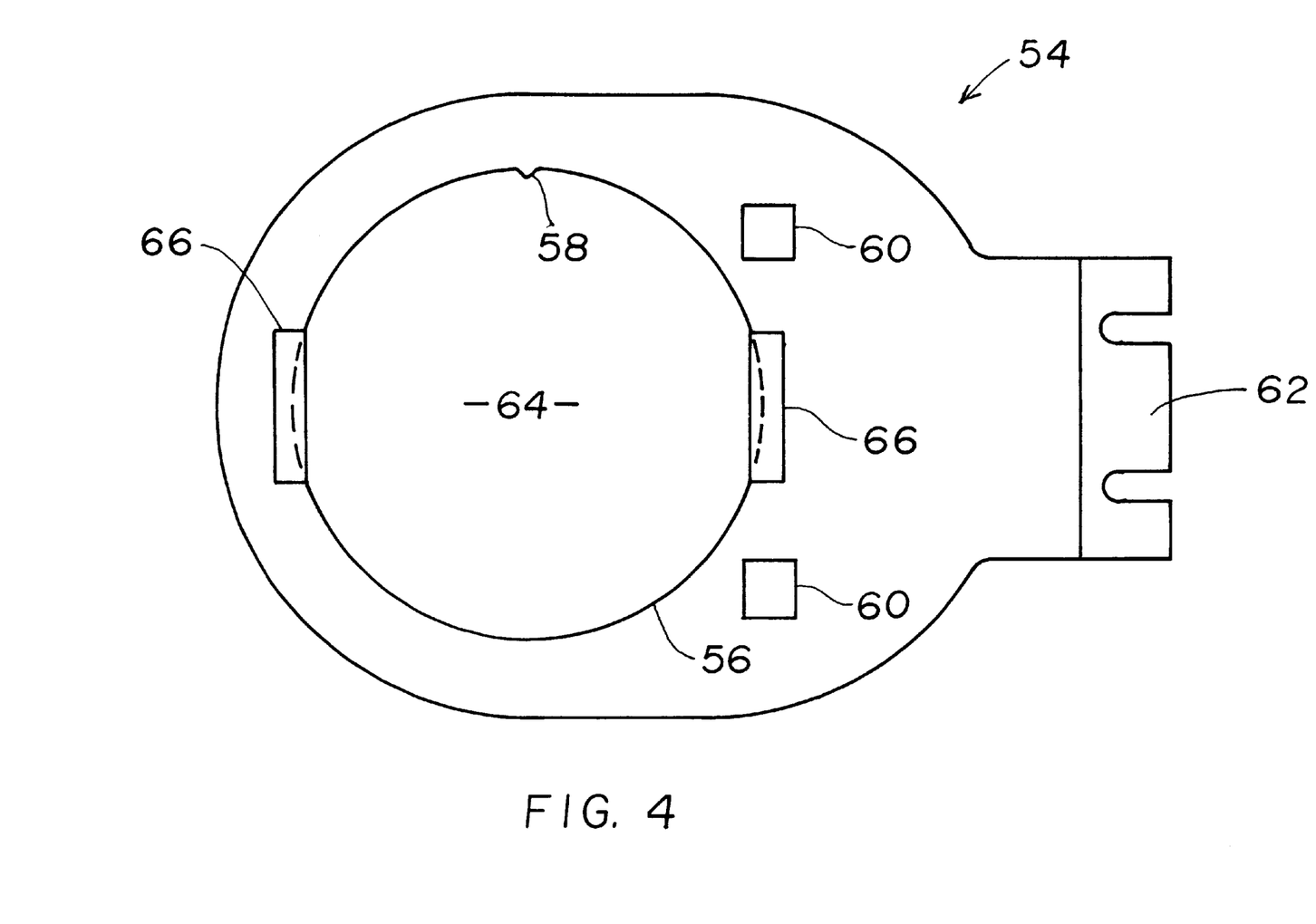
FIG. 4 shows the tray of FIG. 3 with a wafer retained in place by magnets overlapping the wafer's edges.

The material of the tray 54 is selected so as to provide minimal sliding friction in contact with the flat supporting plate 46 (FIG. 2), which is preferably made of steel and machined to near perfect flatness and smoothness. Thus, the tray 54 can be moved smoothly, rapidly and precisely over the plate 46 to position any portion of the wafer housed in the opening 56 within the field of view of the IR microscope 50 through the window 48. For that purpose, the tray 54 is also provided with a clamp 62 for connection with an x,y translation and rotation mechanism operating over the support plate 46. I found that the G-10 fiberglass material used in the industry for printed circuit boards is very suitable for practicing the invention. As shown in FIG. 4, a wafer 64 is placed into the opening 56 as a removable insert, aligned within the opening by the protrusion 58, and it is secured in place by a retaining means 66 adapted to apply sufficient pressure on the wafer to maintain its firm engagement within the tray 54. Due to the almost frictionless sliding capability of the tray 54 over the support plate 46, the retaining means can simply consist of adhesive tape or, preferably, flexible magnets overlapping the abutting edges of the wafer 64 and the opening 56. Since the plate 46 is preferably made of steel, magnets will be attracted to it and apply a downward force sufficient to keep the wafer in place while free to slide with the wafer and tray over the plate.

Figure 5:
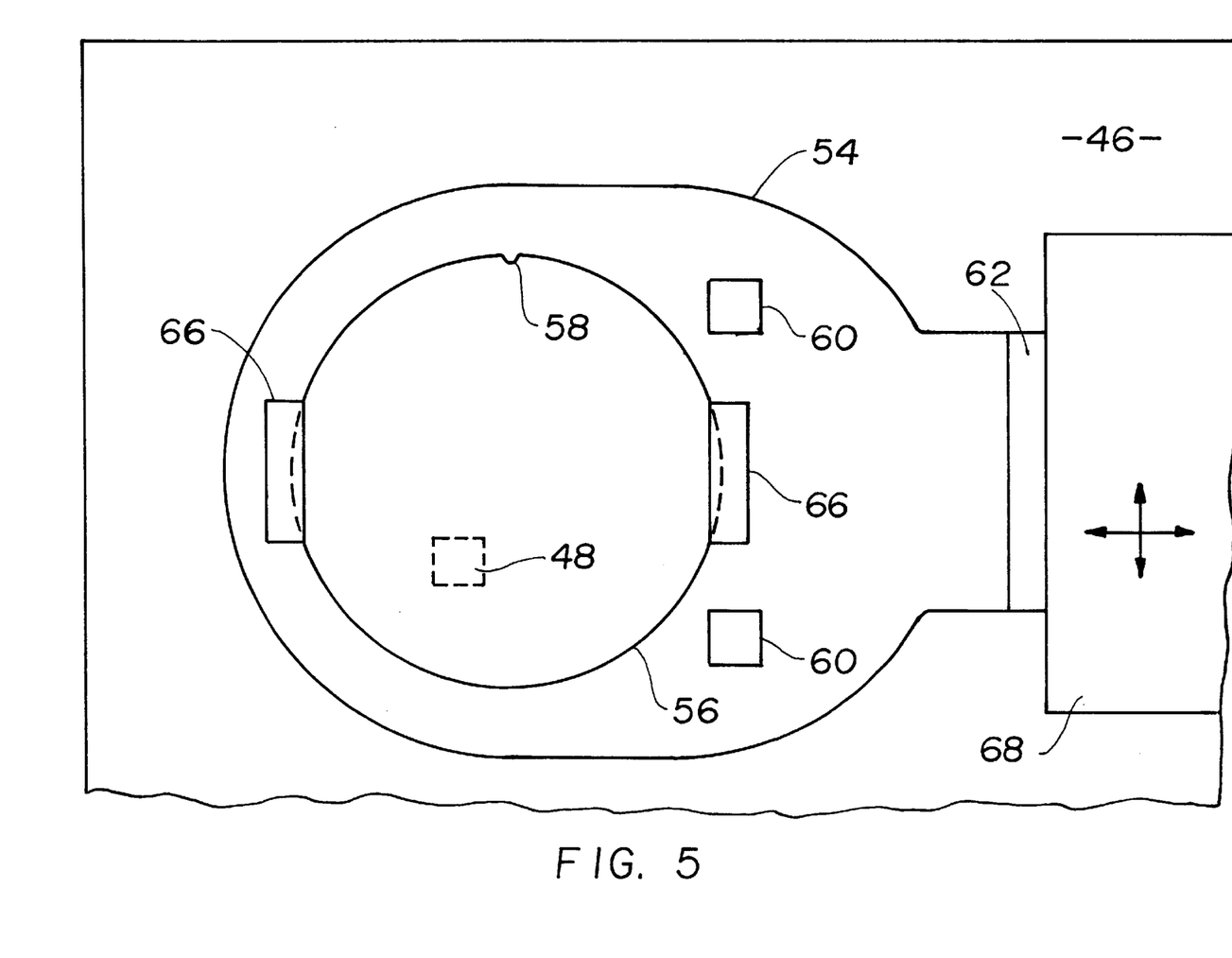
FIG. 5 illustrates the placement of a particular integrated circuit in a wafer over the window of a support plate for back-side imaging with an infrared microscope according to the invention.
Figure 6:
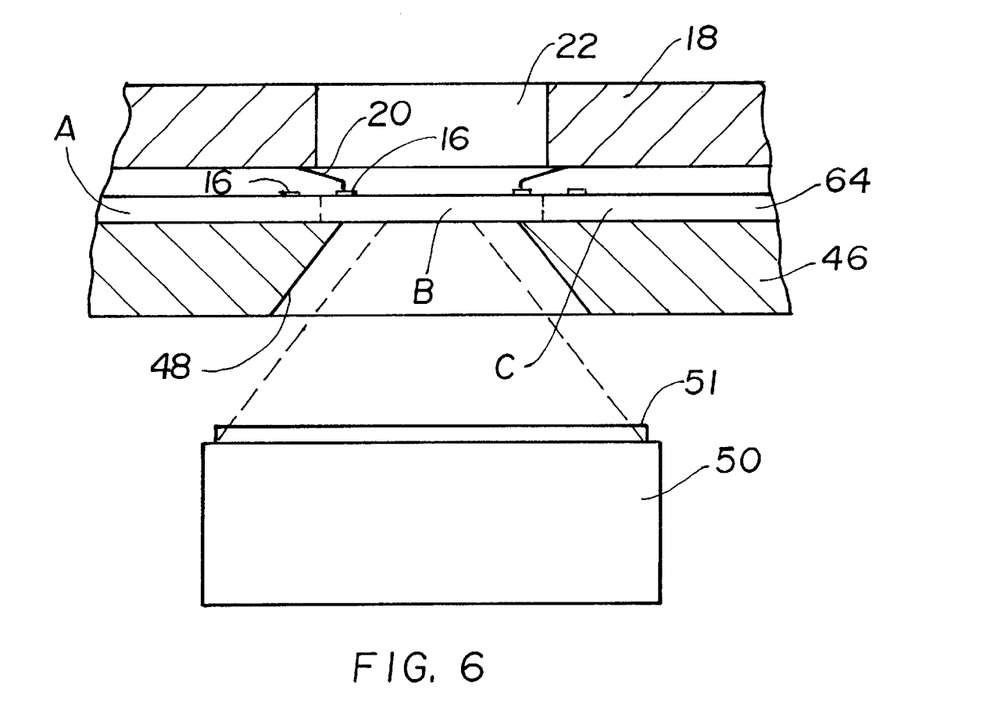
FIG. 6 is a partially sectioned elevational view of a wafer positioned with a particular integrated circuit over the window of the support plate such that the IC contact pads and the tips of the probe card are substantially aligned with the edge of the window.

FIG. 5 illustrates in top view the way the silicon wafer is positioned over the window 48 of the support plate 46 in order to implement the back-side imaging concept of the invention. Using the x,y translation and rotation mechanism 68, the tray 54 is translated over the support plate 46 to position a particular portion of the wafer over the window 48 (shown in phantom line) below the wafer. Since the purpose of the instrument is to test one integrated circuit at a time, the window 48 is preferably only sufficiently large to expose a single circuit and its contact pads and as little additional surface as possible. This window size ensures maximum support of the wafer, whose portion under test may remain unsupported, and minimizes structural stresses that can damage the chips, especially when pressure is applied to the contact pads by the tips 30 of the probe 20 (see FIG. 1). Accordingly, the shape of the window (shown as square for example in the figure) is also preferably selected to conform to the pattern of the contact pads in the integrated circuits under testing. By aligning the pads with the edge of the window 48, as illustrated in the sectioned elevational view of FIG. 6, the probe tips, the pads and the integrated circuit can be fully viewed with the underlying IR microscope 50 while maximum support is provided to the structure of the wafer 64. The figure illustrates a sequence of adjacent ICs (A, B and C) in the wafer, B being the one currently viewed.

Note that for very large integrated circuits and highly thinned wafers more support under the chip may be needed. Accordingly, a thin polished and AR-coated layer such as glass or sapphire may be inserted in the window, causing only a slight loss in performance. Thus, both open and filled windows may be used to implement the invention, as required by the size and thickness of specific integrated circuits.

Figure 7:
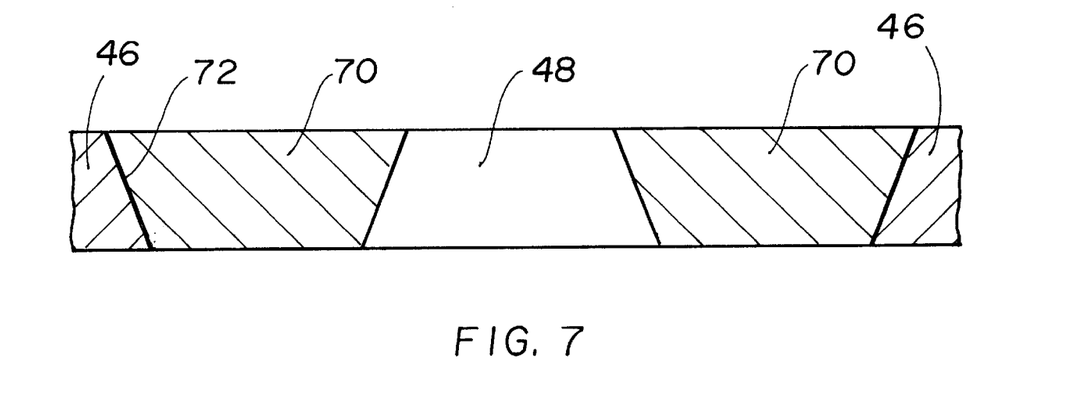
FIG. 7 is a sectioned elevational view of a removable insert used to form a window in the support plate of the invention.

In order to accommodate different chip geometries and dimensions, multiple shapes and sizes of the window 48 can be provided by using inserts that fit within a single large opening in the plate 46. For example, as shown in FIG. 7, an insert 70 is fitted into a large opening 72 in the support plate 46 to provide a window 48 of a particular shape and size, which can obviously vary at will as needed to match the geometry of the integrated circuit being tested. Thus, a set of inserts 70 can be used to adapt the support plate to optimally test wafers carrying any size and shape of chip. In the preferred embodiment of the invention, the inserts 70 are made of the same low-friction material used for the tray 54, thereby further reducing friction between the two and enhancing the ease with which the tray can be moved as it slides over the support plate 46.

Figure 8:
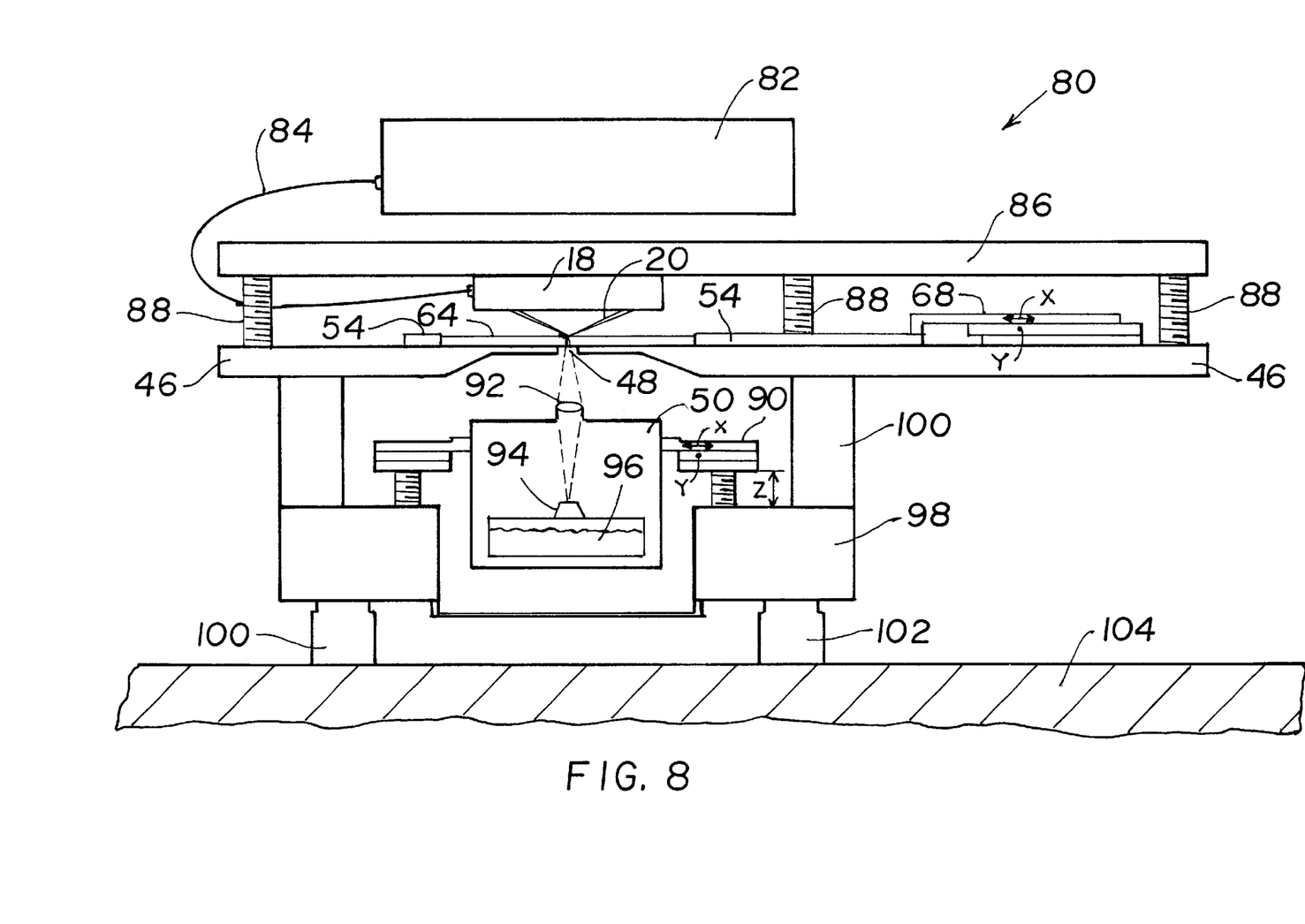
FIG. 8 is a schematic representation of the preferred embodiment of invention.

The preferred embodiment of the invention is shown schematically in FIG. 8, where it is fully integrated with a testing device such as the IREM1™. Such probe station 80 includes a probe card 18 with probes 20, as described connected in conventional manner to a remote electronic tester 82 via a cable 84. The card 18 is attached to a platen 86 and includes a mechanism 88 for raising and lowering the probes 20 between tests of individual ICs. The platen 86 is connected to the support plate 46 of the invention through three separate supports 88 of variable length that provide a way to adjust the attitude of the platen 86 with respect to the plate 46 and ensure that the probes 20 are parallel to the contact pads of the circuit being tested. Each support 88 can consist simply of a precision jack screws that can be turned manually to change the length of the support. Preferably, the supports include manual or automated mechanisms that can be operated to provide the desired parallelism in response to electronic input resulting from the infrared images generated by the IR microscope of the invention.

As explained above, the plate 46 supports the wafer tray 54 of the invention with a wafer 64 inserted therein for testing. The tray 54 is attached to the x,y translation and rotation mechanism 68 for positioning the wafer as desired over the bottom window 48 of the support plate 46. The infrared camera 50 of the invention, including conventional microscope optics 92 and a detector array 96 passively cooled by liquid nitrogen, is positioned below the window 48. The camera 50 is fitted with an x,y,z translation mechanism 90 appropriate for aligning and focusing the camera, as needed. The plate 46 and camera 50 are connected by rigid frame components 98,100 supported in conventional manner by pneumatic supports 102 over a firm floor 104 in order to minimize vibrations in the system.

In operation, a silicon wafer containing a plurality of integrated circuits in well defined positions within the wafer is placed in the tray 54 of the invention. With appropriate calibration of the system carried out using conventional control and positioning apparatus, each integrated circuit in the wafer can be identified and positioned exactly with respect to predetermined reference coordinates. Therefore, all circuits in the wafer can be tested automatically in sequence or any particular circuit can be selected for individual testing. In either case, the wafer is moved to position the integrated circuit of interest over the window of the support plate 46 and in vertical alignment with the fingers of the probe card. The IR camera below the support plate is used to control the alignment process by imaging the probe tips and contact pads through the silicon substrate with infrared light. When electrical contact is established, the circuit is energized for testing with the probe card and, at the same time, any infrared emission resulting from failures is imaged from the bottom side of the wafer with the IR camera of the invention. Thus, any emission caused by hot-carrier or electrical-short faults is detected and used to isolate and identify the source of the failure.

It is noted that current silicon wafers are about 200–700 microns in thickness. Those substrates that are sufficiently transparent to IR wavelength allow the direct and immediate imaging of the probe tips as soon as the probe card has been lowered into position just above the front-side surface of the wafer. Fully transparent areas normally exist between adjacent circuits in the wafer and can be used to view the probe tips. In any event, transparent open areas are always present near the wafer's edge. Alternatively, the probe tips can be imaged through the openings 60 or prior to inserting the wafer in the tray of the invention. Once the location of a few selected tips (a pair is enough to locate a known pattern) is established within the reference framework of the system, the x,y position of the wafer can be adjusted within short travel distances to produce a substantially perfect alignment of the tips with the contact pads of a selected circuit of known position within the wafer. The arrangement of the invention, in which the wafer is supported and imaged from one side while the electrical contacts are made from the opposite side, provides a common reference frame for precise x,y,z position measurements, which are essential to a successful alignment operation. Tests have shown that this critical probe/pad alignment can be accomplished within a tolerance of +/−4 microns using the IR microscope of the invention in combination with conventional translation and control apparatus.

Figure 9:
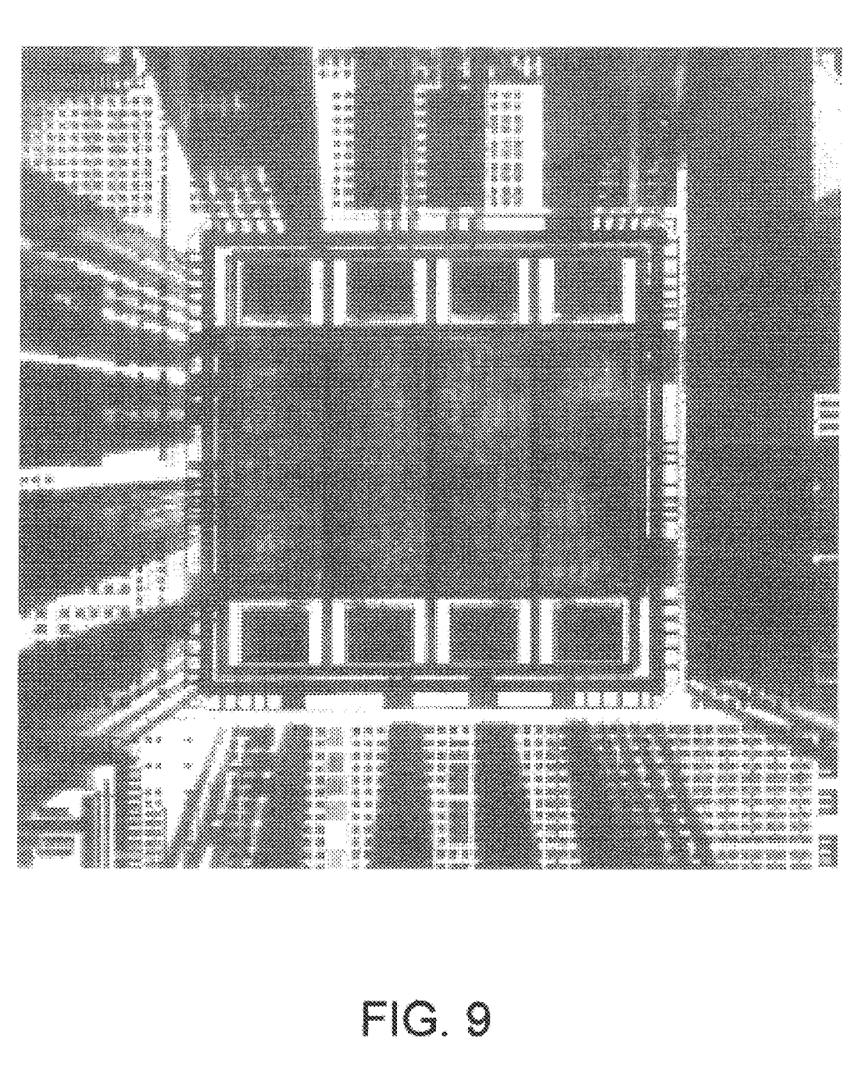
FIG. 9 is an infrared image illustrating the alignment of probe tips with contact pads of a chip using the apparatus of the invention.
Figure 10:
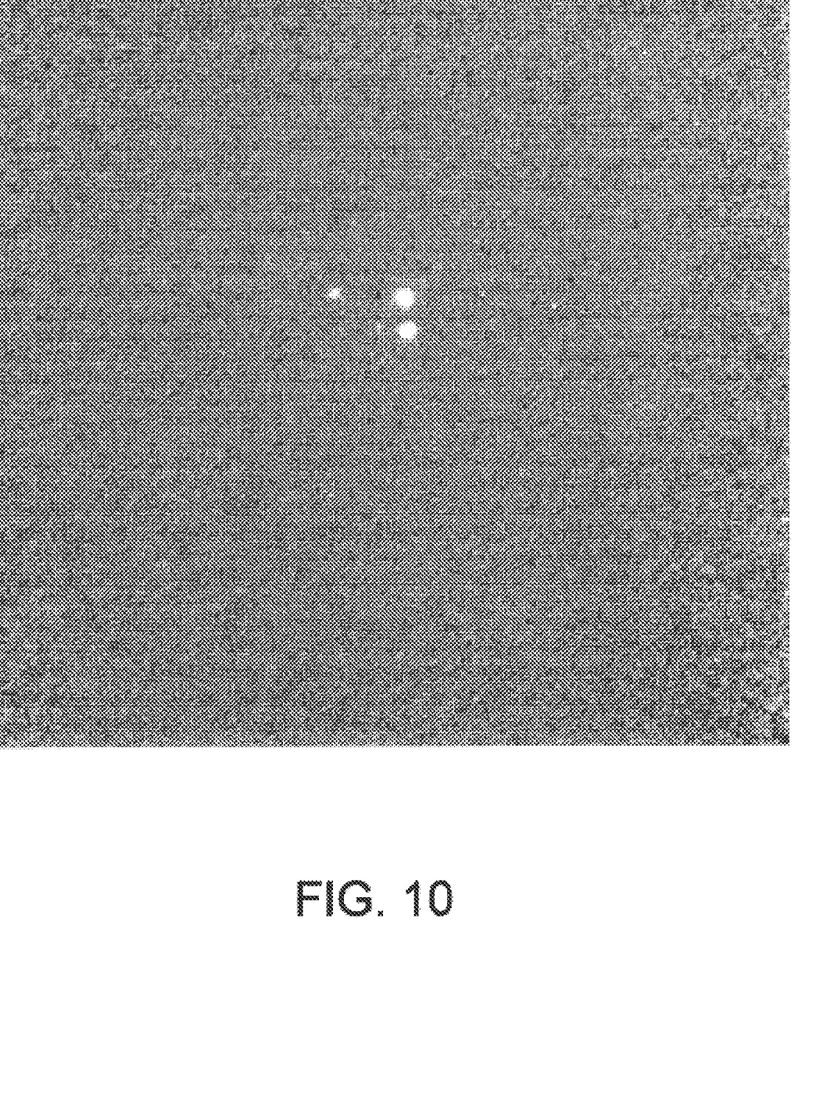
FIG. 10 is an image illustrating the infrared emission of a failure spot in an integrated circuit revealed using the back-side imaging apparatus of the invention without illumination.

FIGS. 9 and 10 illustrate the type of images produced by the infrared device of the invention. FIG. 9 shows the process of alignment of the finger tips of a probe card with the contact pads of an integrated circuit of a wafer. FIG. 10 illustrates the IR emission corresponding to a circuit failure as captured by the camera of the invention positioned below the silicon substrate of the wafer. Note that only the emission spot is seen in the figure because no illumination light is used.

The device and method of the invention provide several advantages over the prior art. The high precision of alignment derived from back-side imaging through the silicon substrate reduces the force applied to the wafer by the probe card, thereby also reducing the probability of undesirable deformation of the wafer and/or probe card. As technological advances produce thinner and thinner wafers, this characteristic of the invention may prove to be critical to avoid damaging wafers during testing. With current wafers, the novel testing stage of the invention makes it possible to test an entire wafer, rather than only a single packaged chip. Furthermore, the need for top-side imaging through the probe card is completely eliminated; thus, the latest type of "flip-chip" probe card with contacts located throughout the interior of the chip can be aligned using the apparatus and procedure of the invention.

Various changes in the details, steps and components that have been described may be made by those skilled in the art within the principles and scope of the invention herein illustrated and defined in the appended claims. For example, fractional or partial wafers will be tested with this invention as easily as are whole wafers. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

I claim:

1. Apparatus for testing an integrated circuit on a silicon wafer by infrared emission microscopy comprising:
   a support plate with a window;
   a stage for receiving the silicon wafer and positioning the integrated circuit over said window;
   a probe card with probe tips positioned over the window;
   means for aligning the probe tips with contact pads in said integrated circuit; and
   an infrared emission camera positioned under said window with a field of view encompassing the probe tips and the contact pads.

2. The apparatus of claim 1, wherein said window in the support plate is contained in a removable insert placed within the plate.

3. The apparatus of claim 1, wherein said window in the support plate includes a transparent layer to provide further support to the integrated circuit.

4. The apparatus of claim 1, further comprising means for adjusting the x,y and rotational attitude of the probe card with respect to the support plate.

5. The apparatus of claim 1, further comprising means for raising or lowering the probe card with respect to the integrated circuit while maintaining a predetermined x,y and rotational attitude of the probe card with respect to the support plate.

6. Apparatus for testing a silicon wafer by infrared emission microscopy comprising:
   a support plate with a window;
   a tray for receiving and securely retaining a silicon wafer in fixed relation to the tray, said tray being slidably coupled to the plate and to a positioning mechanism for placing a selected portion of the wafer over said window;
   a probe card with probe tips positioned over the window;
   means for aligning the probe tips with contact pads of an integrated circuit in said selected portion of the wafer; and
   an infrared emission camera positioned under said window with a field of view encompassing the probe tips and the contact pads.

7. The apparatus of claim 6, wherein said window in the support plate is contained in a removable insert placed within the plate.

8. The apparatus of claim 7, wherein said insert and tray are made of the same material.

9. The apparatus of claim 6, wherein said window in the support plate includes a transparent layer to provide further support to the integrated circuit.

10. The apparatus of claim 6, wherein said tray comprises an opening conforming to the size of the wafer.

11. The apparatus of claim 10, further comprising means for aligning the tray with a conforming alignment notch in the wafer.

12. The apparatus of claim 10, further comprising retaining means for securing the wafer in place within the opening.

13. The apparatus of claim 12, wherein said retaining means includes a magnet.

14. The apparatus of claim 6, further comprising means for adjusting the x,y and rotational attitude of the probe card with respect to the support plate.

15. The apparatus of claim 6, further comprising means for raising or lowering the probe card with respect to the integrated circuit while maintaining a predetermined x,y and rotational attitude of the probe card with respect to the support plate.

16. A method of testing an integrated circuit by infrared emission microscopy comprising the steps of:
   (a) providing a support plate with a window;
   (b) providing a tray for receiving and securely retaining an integrated circuit in fixed relation to the tray;
   (c) placing the integrated circuit and corresponding contact pads over said window;
   (d) positioning a probe card with probe tips over the window;
   (e) providing an infrared emission camera positioned under the window with a field of view encompassing the probe tips and the contact pads;
   (f) imaging said probe tips and the integrated circuit with the infrared emission camera in order to effect an alignment and electrical contact between the probe tips and the contact pads in the integrated circuit;
   (g) energizing the probe card to test the integrated circuit; and
   (h) imaging the integrated circuit with the infrared emission camera to detect and isolate infrared emissions corresponding to circuit failures.

17. The method of claim 16, wherein said tray includes means for receiving and securely retaining a silicon wafer in fixed relation to the tray; the tray is slidably coupled to the plate and to a positioning mechanism for placing a selected portion of the wafer over said window; and step (c) consists of placing said selected portion of the wafer with an integrated circuit and corresponding contact pads over the window.

18. The method of claim 17, further comprising the steps of:
   (i) moving the tray to place a new integrated circuit with corresponding new contact pads over the window; and
   (j) repeating steps (f)–(h) to test said new integrated circuit.

19. The method of claim 18, wherein steps (i) and (j) are carried out automatically.

20. A method for aligning probe tips of a probe card with contact pads of an integrated circuit for conducting failure analysis, comprising the following steps:
   providing an infrared emission camera positioned under the integrated circuit with a field of view encompassing the probe tips and the contact pads;
   imaging the probe tips and the integrated circuit with the infrared emission camera; and
   effecting a relative position of the probe tips and the integrated circuit such as to produce alignment and electrical contact between the probe tips and the contact pads in the integrated circuit.

* * * * *